(12) United States Patent
Kindlein

(10) Patent No.: US 7,027,560 B2
(45) Date of Patent: Apr. 11, 2006

(54) CRYOGENIC X-RAY SOURCE DEVICE

(75) Inventor: Johann Kindlein, Toenisvorst (DE)

(73) Assignee: Nucletron B.V., Veenendaal (NL)

( * ) Notice: Subject to any disclaimer, the term of this patent is extended or adjusted under 35 U.S.C. 154(b) by 0 days.

(21) Appl. No.: 10/871,055

(22) Filed: Jun. 21, 2004

(65) Prior Publication Data

US 2005/0025285 A1 Feb. 3, 2005

(30) Foreign Application Priority Data

Jun. 30, 2003 (EP) ................................ 03077134

(51) Int. Cl.
*H01J 35/12* (2006.01)
(52) U.S. Cl. ...................... 378/141; 378/122
(58) Field of Classification Search ................ 378/119, 378/121, 122, 136, 141, 199, 200; 250/370.15; 600/2, 3, 433, 435, 466; 604/20, 264
See application file for complete search history.

(56) References Cited

U.S. PATENT DOCUMENTS

| | | | | |
|---|---|---|---|---|
| 3,942,010 A | * | 3/1976 | Peterson et al. | ............ 250/352 |
| 6,208,706 B1 | * | 3/2001 | Campbell et al. | ............... 378/9 |
| 6,319,188 B1 | * | 11/2001 | Lovoi | ............................ 600/3 |
| 2002/0049436 A1 | | 4/2002 | Zvuloni et al. | ................ 606/21 |

FOREIGN PATENT DOCUMENTS

| | | |
|---|---|---|
| DE | 19826000 C1 | 12/1999 |
| JP | 61-107642 A | 5/1986 |
| JP | 61107642 A * | 5/1986 |

* cited by examiner

*Primary Examiner*—Edward J. Glick
*Assistant Examiner*—Courtney Thomas
(74) *Attorney, Agent, or Firm*—Birch, Stewart, Kolasch & Birch, LLP

(57) ABSTRACT

The invention relates to a miniature X-ray source device connected to a distal end of a guiding wire for insertion towards a desired location within an animal body for effecting radiation therapy, said X-ray source device at least comprising a vacuum tube accommodated in said housing containing a cathode and an anode spaced apart at some distance from each other; electron freeing means for freeing electrons from the cathode; electric field means for applying during use a high-voltage electric field between said cathode and said anode for accelerating said free electrons; said vacuum tube being at least partly transparent to X-ray radiation emitted by said anode, as well as cooling means for cooling at least said anode.

Figure 1:
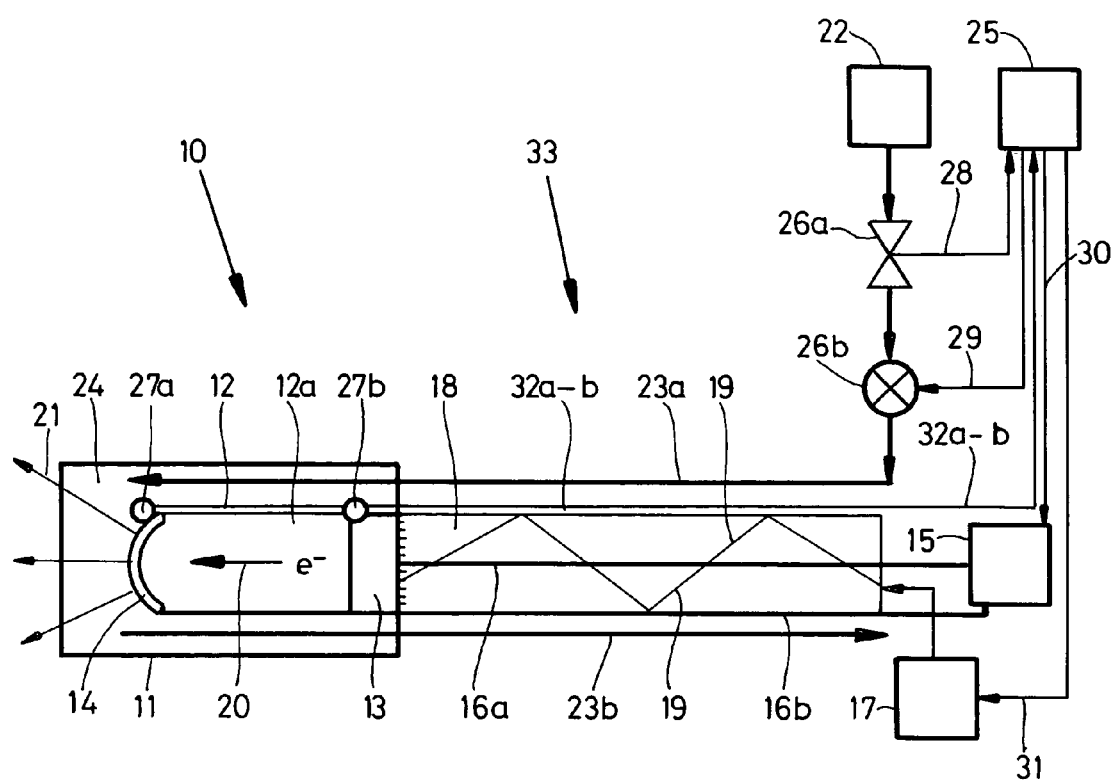

It is an object to provide a miniature X-ray source device having further limited constructional dimensions and an improved control of the working temperature of at least the anode and hence the working conditions of the miniature X-ray source device.

According to the invention the miniature X-ray source device is hereto characterised in that said cooling means are cryogenic cooling means. More in particular in a specific embodiment of said miniature X-ray source device said cooling means comprise at least one supply passageway for supplying pressurized gas towards said anode and at least one exhaust passageway for exhausting said pressurized gas from said anode, said supply passageway and said exhaust passageway being interconnected by means of an expansion chamber surrounding at least partly said anode.

27 Claims, 3 Drawing Sheets

CRYOGENIC X-RAY SOURCE DEVICE

This Non-provisional application claims priority under 35 U.S.C. § 119(a) on Patent Application No(s). 03077134.9 filed in Europe on Jun. 30, 2003, the entire contents of which are hereby incorporated by reference.

BACKGROUND OF THE INVENTION

1. Field of the Invention

The invention relates to a miniature X-ray source device connected to a distal end of a guiding wire for insertion towards a desired location within an animal body for effecting radiation therapy, said X-ray source device at least comprising a vacuum tube accommodated in said housing containing a cathode and an anode spaced apart at some distance from each other; electron freeing means for freeing electrons from the cathode; electric field means for applying during use a high-voltage electric field between said cathode and said anode for accelerating said free electrons; said vacuum tube being at least partly transparent to X-ray radiation emitted by said anode, as well as cooling means for cooling at least said anode.

The present invention relates to a generation of X-rays for medical purposes, and in particular it relates to miniature X-ray source device for intravascular treatment of lesions in body tissue, in particular for treatment of stenosis in coronary vessels and the treatment of cancer tumours.

2. Description of the Related Art

Radiation therapy is a well-established method for treatment of several diseases, including cancer. The presumptive usefulness of a miniature X-ray source device is clear. The insertion of such a source device into vessels or other body cavities would allow the delivered radiation dose to be confide to a small tissue region. More specific, a catheter with a miniaturized X-ray source device could be used for irradiation of cardiovascular tissue.

A miniature X-ray source device according to the above preamble is for example known from U.S. Pat. No. 6,319,188 B1. In this patent publication an embodiment of an X-ray source device is disclosed, having a cylindrically-shaped vacuum tube, wherein a cathode and an anode spaced apart are accommodated. The anode is mounted on a distal end of said miniature X-ray source device.

The vacuum tube is to be evacuated to a preferred vacuum level required for a proper operation of the miniature X-ray source device. Furthermore, the known miniature X-ray source device is provided with electric field means for establishing a high-voltage electric field between the anode and cathode. Electrons emitted from said cathode are accelerated by said established high-voltage electric field and impact with a high kinetic energy on said anode material. In the anode material X-ray radiation is generated with a high energy level.

As the vacuum tube is entirely highly transparent to X-ray radiation, said generated radiation can leave the vacuum tube towards the patient's tissue in which the X-ray source device is inserted. AS the generated X-ray radiation leaving the miniature X-ray source device exhibits a high energy level, the X-ray radiation is highly suitable for performing radiation therapy in said patient's body, for example for treating cancer tumours.

However, upon impact of the free electrons emitted from the cathode and accelerated towards the anode, only a small amount of the kinetic energy of said electrons is converted into X-ray radiation. A significant large amount is converted into heat significantly increasing the working temperature of the anode. Due to the rather small dimensions of the X-ray source device as well as due to the environment (the patient's body) in which the X-ray source device is used and also in order to extend the life span of the device it is necessary to cool the anode to a proper working temperature.

In U.S. Pat. No. 6,319,188 it is suggested to use an open ended system or a closed loop system comprising a thin sheath of a cooling liquid transported over the cable and X-ray tube. Although with such cooling means a higher rate of heat dissipation and subsequently a decrease in the working temperature of the anode can be obtained they require significant cooling capacity of the cooling means before an efficient cooling of the anode is obtained. Furthermore with a construction like suggested in U.S. Pat. No. 6,319,188 the outer dimensions of the X-ray source device are increased, further limiting the application of such a device in the patient's body.

Furthermore, in the known miniature X-ray source device provided with cooling means an accurate control of the cooling means in order to establish a desired temperature of the anode and thus of the operational conditions of the miniature X-ray source device is not possible.

SUMMARY OF THE INVENTION

It is an object of the present invention to provide a miniature X-ray source device according to the above preamble having further limited constructional dimensions and an improved control of the working temperature of the anode and hence the working conditions of the miniature X-ray source device.

According to the invention the miniature X-ray source device is hereto characterised in that said cooling means are cryogenic cooling means.

More in particular in a specific embodiment of said miniature X-ray source device said cooling means comprise at least one supply passageway for supplying pressurized gas towards said anode and at least one exhaust passageway for exhausting said pressurized gas from said anode, said supply passageway and said exhaust passageway being interconnected by means of an expansion chamber surrounding at least partly said anode.

With these two features an adequate supply of cooling medium in the form of pressurised gas can be supplied to the anode, whereas the cooling and hence heat dissipation takes place due to the gas expansion within the expansion chamber. Expansion of pressurised gas results in a drop in the internal temperature of said gas allowing an improved cooling of the anode towards an acceptable and optimal lower working temperature.

The heat dissipated from said anode and absorbed by said cooling medium can be removed from the miniature X-ray source device via said exhaust passageway.

In an improved embodiment wherein also a cooling effect of the cathode and the vacuum tube is established said miniature X-ray source device according to the invention is characterised in that said at least one exhaust passageway is accommodated in one or more helical X-ray transparent windings around said vacuum tube.

A further improvement in the cooling capabilities of the miniature X-ray source during operation can be established whereas said cooling means comprise two supply passageways.

More in particular said at least one supply passageway has an outer diameter of 0.2–0.01 mm and an inner diameter of 0.17–0.005 mm, resulting in a further reduction of the outer constructional dimensions of the miniature X-ray source device and thus further improving the insertion, displacement and use of such miniature X-ray source device within a patient's body.

In further advantageous embodiment said exhaust passageway is formed by an interstice present between said housing and said vacuum tube, wherein furthermore said interstice at least partly surrounds said vacuum tube or wherein said interstice at least partly surrounds said at least one supply passageway.

In order to allow an advantageous control of the working or operational temperature of the anode or cathode in a preferred embodiment a thermo-sensor is positioned near said anode to monitor the temperature of the anode and/or a thermo-sensor is positioned near said cathode to monitor the temperature of the cathode.

More in particular said thermo-sensor is one of the group of a miniaturized thermocouple, diode or transistor device. These embodiments of the thermo-sensor are known for their quick response due to temperature changes and require a limited constructional space within the miniature X-ray source device. The latter further improves the insertion and use of such source device within the patient's body.

Preferably said gas used as a cooling medium is selected from a group consisting of argon (Ar), nitrogen ($N_2$), air, krypton (Kr), $CF_4$, Xenon (Xe) and $N_2O$.

More in particular in a preferred embodiment said electron freeing means comprise an optical fibre connecting said cathode to a light emitting source, wherein preferably said light emitting source is controllable. In specific embodiments the miniature X-ray source device is characterised in that said light emitting source is a laser device, a LED or the like. With these features the operation of the cathode and more in particular the free electron flux emitted by the cathode material in the direction of the anode of X-ray radiation generated within the anode material can be properly controlled. This allows a more sophisticated and advanced operation of the miniature. X-ray source device according to the invention. In fact for radiotherapy purposes stable voltage and stable current properties are essential to assure a predefined and well-determined radiation dose distribution emitted by said anode.

In another preferred embodiment said electric field means comprises a high-voltage conductor connecting said cathode to a high voltage supply and said anode to ground potential, wherein for obtaining a further reduction in the constructional dimensions said high voltage conductor is embedded in said optical fibre.

It is preferred to use a cathode which is of a field-emitting type. More particularly said cathode is a cold cathode, wherein in the specific embodiment said cathode is a cold cathode made of carbon nanotube material.

By controlling the working (operational) temperature of the cathode an effective control can be obtained of the electron flux emitted from said cathode material as well as the X-ray radiation flux emitted by said anode material.

To this end it is possible to control the miniature X-ray source device as regard to the X-ray radiation emitted towards the patient's body wherein radiation therapy treatments are to be performed. More in particular with the X-ray source device according to the invention a generated and emitted radiation dose distribution accurately matching the desired preplanned radiation dose distribution is possible.

This results in an improved and sophisticated and well-controlled miniature X-ray source device furthermore having limited constructional dimensions. In another embodiment according to the invention said miniature X-ray source device is characterised in that said vacuum tube further comprises a wehnelt cylinder mounted around said cathode. The use of a getter-material is intended to absorb or eliminate stray gas molecules still present in the evacuated vacuum tube therefore further improving the vacuum level of the miniature X-ray source device.

With this embodiment wherein the getter material is positioned on the outer or inner surface of the wehnelt cylinder the getter material is not adversely affected by the high voltage electric field generated between the anode and the cathode and hence any internal electrical problems associated with surface arcing or breakdown of the getter material is herewith avoided.

Preferably said vacuum tube is made of alumina, sapphire, diamant or silica.

In another preferred embodiment said miniature X-ray source device according to the invention is characterised in that it further comprises control means for controlling said electric field generating means, said electron freeing means and said supply of pressurised gas towards the anode.

More in particular, said control means are arranged to control the temperature of said cathode and/or anode using said electric field generating means, said electron freeing means, said supply of pressurized gas and said thermo-sensors.

With these features an improved miniature X-ray source device according to the invention is obtained having more sophisticated possibilities in controlling the temperature of the anode and/or cathode and thus the electron flux emitted by said cathode and the X-ray radiation flux emitted by said anode.

The invention also relates to a method for effecting radiation therapy in an animal body using a miniature X-ray source device according to anyone of the preceding claims.

BRIEF DESCRIPTION OF THE DRAWING FIGURES

Figure 2:
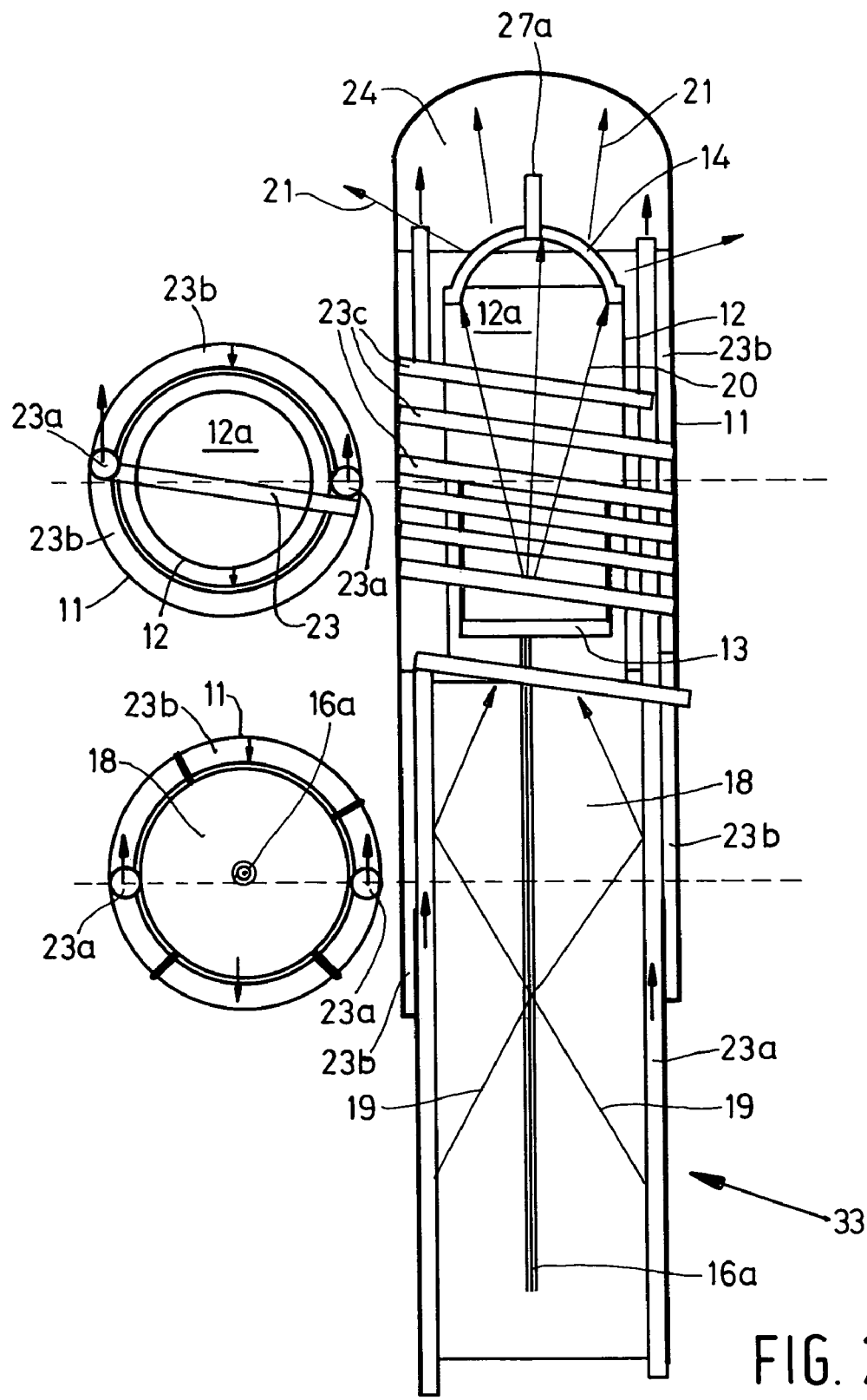
Figure 3:
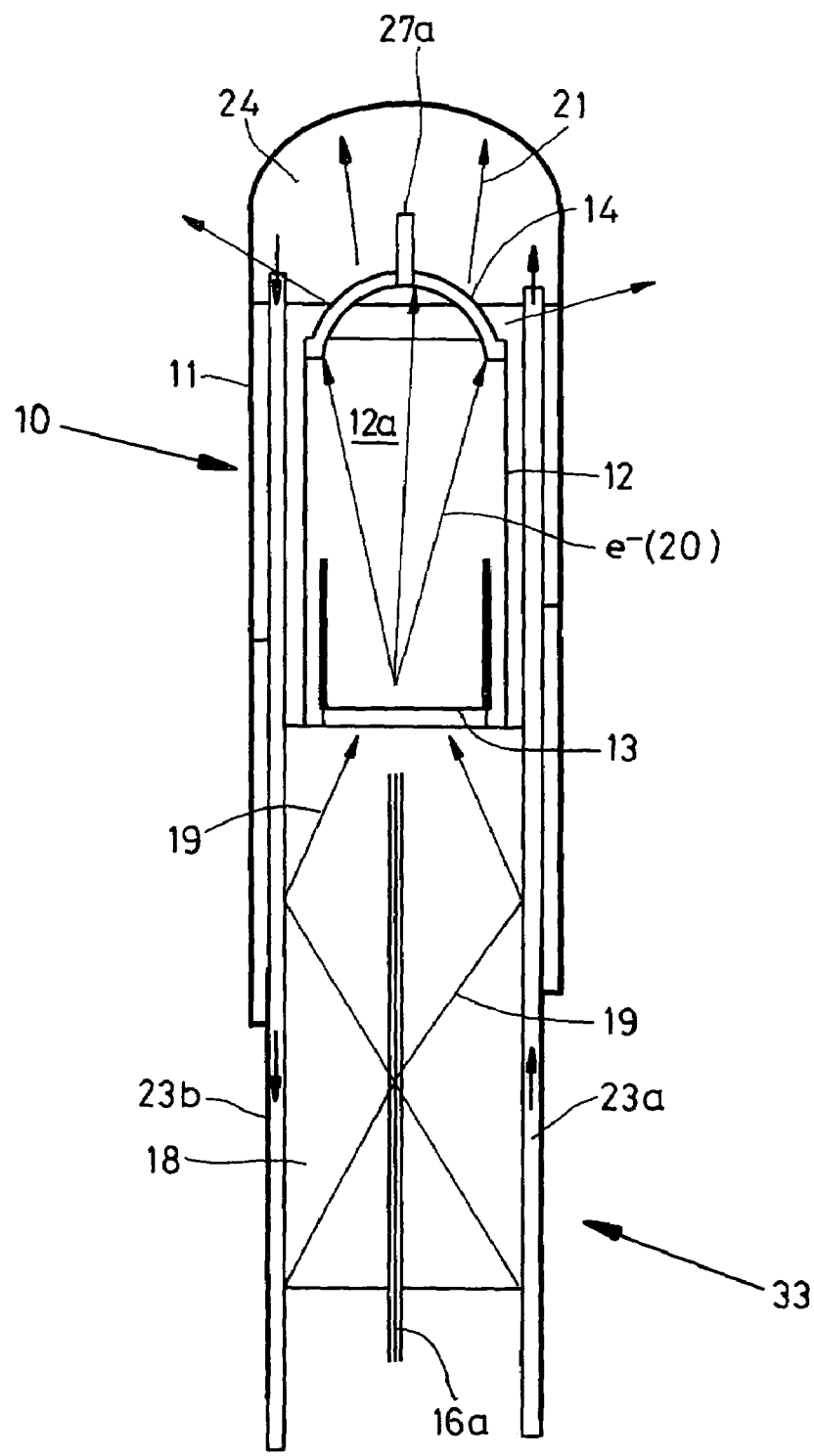

The invention will now be described or in more detail with reference to a drawing which drawing shows in:

FIG. 1 a first embodiment of a miniature X-ray source device according to the invention;

FIG. 2 a second embodiment of a miniature X-ray source device according to the invention;

FIG. 3 a third embodiment of a miniature X-ray source device according to the invention.

In the following detailed description with reference to the accompanying Figures identical components of the embodiments shown will be indicated with identical reference numerals.

DETAILED DESCRIPTION

In FIG. 1 a first embodiment of miniature X-ray source device according to the invention is disclosed. The miniature X-ray source device 10 comprises a housing 11 wherein a vacuum tube 12 is accommodated. Within said vacuum tube a cathode 13 and an anode 14 are positioned at some distance from each other. The vacuum tube 12 forms a cavity or chamber 12*a* which is evacuated to a desired vacuum level necessary for a proper operation of the miniature X-ray tube.

The cathode 13 is connected to light emitting means 17 in this embodiment constructed as a laser device or LED device or a similar light emitting component. These means emits a light beam 19 which travels through an optical fibre 18 of a considerable length which is connected to the cathode 13.

The light 19 emitted by said light-emitting means 17 impinge on the cathode 13 and free electrons 20 are emitted from said cathode material 13.

The miniature X-ray source device 10 is also provided with electric field generating means 15 for applying during use a high-voltage electric field between said cathode 13 and said anode 14 positioned at some distance from each other. Thereto said electric field means comprise a high-voltage source 15 connected via a high-voltage cable 16 with the cathode 13. Likewise the anode 14 is connected via an electrical conductor 16b preferably to ground potential. By applying a high negative voltage to said cathode 13 free electrons e⁻ emitted from the cathode material based on the photoelectric effect or the field emission effect are accelerated in form of an electron flux J (20) towards the anode 14.

The accelerated electrons 20 impact with a significant high kinetic energy (velocity) on said anode material 14 and in said material 14 X-ray radiation is generated. The X-ray radiation 21 thus generated will leave the housing 11 of the X-ray source device 10 towards the tissue of the patient's body surrounding the miniature X-ray source device 10 for performing radiation therapy treatments. Preferably the vacuum tube 12 and the housing 11 are made at least partly of a material that is transparent to X-ray radiation.

Preferably the cathode 13 is a field emission type cathode as with such type of cathode electrons are emitted from said cathode material and accelerated towards the anode 14 at low temperature instead of in a thermionic activated cathode wherein the cathode material is heated in order to extract electrons from the cathode material. Furthermore, using a field emission type cathode the electron density flux J as emitted is controllable by constant high voltage and variable light flux incidence as generated by the light emitting means 15.

In all of these embodiments a proper control of the electron flux 20 towards the anode 14 is possible allowing a proper control of the X-ray radiation emitted by said anode material.

With this embodiment a cathode 13 is obtained that can deliver a stable electron current 20 towards the anode 14 resulting in a stable and well-determined X-ray radiation dose distribution necessary for performing accurate radiation therapy treatments. In another embodiment the cathode is a cold cathode preferably manufactured of carbon nanotube material. It is established that carbon nanotubes used as a field emitting type cathode can potentially emit a much higher electron emission current, which electron flux 20 is not only highly controllable but also very stable.

The X-ray radiation generated within the anode material 14 and emitted via the vacuum tube 12 and the housing 11 towards the surrounding tissue of the patient's body is however a fraction of the total energy that is converted from the kinetic energy of the electron bombardment emitted by the cathode 13. A larger part of the kinetic energy of the impact electrons 20 is converted into heat thereby raising the working temperature of the anode 14 significantly. A too high working temperature of the anode will eventually result in a melt down or other irreversible damage to the anode material eventually resulting in a complete failure of the miniature X-ray source device.

Cooling of the anode 14 to an appropriate working temperature is therefore necessary and proposals in the field of miniature X-ray source devices are already made. However, these proposals suffer from a lack of sufficient and accurate control of the working temperature of the anode thereby limiting the operation of the miniature X-ray source device within the patient's body significantly.

Furthermore, the known miniature X-ray source devices provided with cooling means for cooling the working temperature of the anode still require significantly large outer dimensions further limiting the use of such miniature X-ray source device within the patient's body.

In FIG. 1 an improvement is disclosed of miniature X-ray source device which is provided with cooling means 22, which are cryogenic cooling means. With reference numeral 22 schematically a supply of pressurised gas is depicted, which pressurised gas is fed through a supply passageway 23 towards the housing 11 of the miniature X-ray source device according to the invention. Within the housing 11 an expansion chamber 24 is accommodated, which chamber is at least partly surrounding said anode 14.

The supply passageway 23a ends within said expansion chamber 24 and pressurised gas supplied from the cooling means 22 through said supply passageway 23a enters the expansion chamber 24 in which an expansion of the pressurised gas occurs immediately resulting in a drop in the temperature of said pressurised now expanded gas.

The drop in the gas temperature caused by the Joule-Thomson effect causes a cooling effect of the anode 14 which is now in thermal contact with the expanded and cooled down cooling gas. To this end the anode 14 is cooled down to an appropriate working temperature, thereby obviating a possible malfunction of the miniature X-ray source device due to a too high working temperature.

The expanded gas exhibiting a temperature drop will absorb the dissipated heat produced by the anode 14 and will leave the expansion chamber 24 through an exhaust passageway 23b towards the cooling means 22 positioned outside the patient's body. There the exhausted gas will be collected and pressurized again and returned towards the expansion chamber 24 as pressurised gas through the supply passageway 23a.

The gas used as a cooling medium is preferably selected from a group consisting of argon (Ar), nitrogen ($N_2$), air, krypton (Kr), $CF_4$, Xenon (Xe) and $N_2O$.

For a proper control of the working temperature of the anode 14 and in another embodiment also a working temperature of the cathode 13 thermo-sensors 27a. (for the anode 14) and 27b (for the cathode 13) are positioned within the housing 11 for monitoring during operation the working temperature of the anode 14 (using the thermo-sensor 27a) and/or the working temperature of the cathode 13 (using the thermo-sensor 27b). Both thermo-sensors 27a–27b are connected via a signal line 32a–32b to control means 25.

In a preferred embodiment requiring a limited outer dimensions the supply passageway 23, the exhaust passageway 23b, the optical fibre 18, the high-voltage supply lines 16a–16b as well as the thermo-sensor signal lines 32a–32b are incorporated in one catheter tube to which the housing 11 of the miniature X-ray source device is connected. The whole assembly (catheter tube with X-ray source device) can be introduced through an intravascular lesion or other passageway through a patient's body towards a location where a radiation treatment has to be performed using the X-ray radiation emitted by the anode 14. The catheter tube 33 thus formed can exhibit a considerable length.

The control means 25 are preferably microprocessor-controlled and are arranged for controlling the electric field generating means 15, the electron freeing means 17 and the supply 22 of cooling medium (pressurised gas) towards the expansion chamber 24. To this end in the supply passageway 23a of cooling medium 22 a pressure sensor 26a is accommodated for measuring the momentaneous pressure of the pressurised gas acting as cooling medium for the anode 14.

The momentaneous pressure value is supplied via signal line 28 towards the control means 25, which control means are arranged for operating a valve 26b via signal line 29 for controlling the supply of pressurised cooling medium (gas) towards the expansion chamber 24. The control means 25 has also an input signal line 32a–32b for obtaining temperature data as measured by the thermo-sensor 27a–27b positioned near the anode 14 and the cathode 13 respectively. Furthermore the control means 25 exhibits output signal lines 30 and 31 for controlling the electric field generating means 15 and the electron freeing means 17 respectively.

According to the invention it is possible to control the working temperature of the cathode 13 and/or the anode 14 by first controlling the supply of cooling medium via valve 26b through supply passageway 23a towards expansion chamber 24 and/or by controlling the electric field generating means 15 which establish an electric field between the cathode 13 and anode 14 and/or by controlling the electron freeing means 17, which means 17 control the free electron flux 20 emitted from the cathode material 13 and accelerated towards the anode material 14.

With this configuration a compact improved miniature X-ray source device 10 according to the invention is obtained allowing a quick and accurate control of the working temperature of the anode 14 and the cathode 13 and hence a proper control of the miniature X-ray source device during operation.

In FIG. 2 a second embodiment of the miniature X-ray source device according to the invention is disclosed wherein the cooling means 22 are not connected by means of a straight supply passageway 23a and a straight exhaust passageway 23b as in FIG. 1 but whereas the supply passageway 23a is accommodated in one or more helical X-ray transparent windings 23c around the vacuum tube 12. This improved embodiment causes also a beneficial cooling effect on the cathode 13 further improving the versatility of the miniature X-ray source device according to the invention but moreover further expanding the life span of the miniature X-ray source device. In this embodiment two supply passageway 23a are used one of the ending straight into the expansion chamber 24 and the other supply passageway 23a accommodated in one or more helical X-ray transparent windings 23c around the vacuum tube 12. The exhaust passageway 23b is in this embodiment formed by an interstice present between the housing 11 and the vacuum tube 12.

Reference is made to the two detailed views of FIG. 2 showing two cross sections at different locations of the miniature X-ray source device.

In a further embodiment as shown in FIG. 2 said interstice 23b partly surrounds at least one passageway 23a to this end both supply passageway and exhaust passageway are in a current manner in heat-exchanging contact further improving the cooling capacity of the cooling means for cooling down the cathode 13 and the anode 14.

Another embodiment is shown in FIG. 3 wherein likewise one straight supply passageway 23a and one straight exhaust passageway 23b is shown interconnected by the expansion chamber 24 partly surrounding the anode 14.

The thermo-sensors 27a–27b used for monitoring the working temperature of the anode and cathode respectively are preferably one of the group of a miniaturized thermocouple, a diode or transistor device.

Furthermore in a specific embodiment the vacuum tube 12 is made of aluminia, sapphire, diamant or silica material, whereas the cathode is made from a material such as tungsten and wherein the anode is made from molybdenum, rhenium, tungsten, copper, rhodium or other typical heavy metal.

It is also an aspect of the invention to dispose the high-voltage supply line 16a concentrically inside the optical fibre 18 and the cooling gas supply/exhaust passageways are embedded on the outside surface of the optical fibre.

It is also possible in a preferred embodiment resulting in a further reduction of the outer dimensions to place the thermo-sensor 27b inside the optical fibre 18 and in direct contact with the cathode 13 in order to accurately monitor the working temperature of the cathode 13.

The invention claimed is:

1. A miniature X-ray source device connected to a distal end of a guiding wire for insertion towards a desired location within an animal body for effecting radiation therapy, said X-ray source device at least comprising:
   a housing;
   a vacuum tube accommodated in said housing containing a cathode and an anode spaced apart at some distance from each other;
   electron freeing means for freeing electrons from the cathode;
   electric field means for applying during use a high-voltage electric field between said cathode and said anode for accelerating said free electrons;
   said vacuum tube being at least partly transparent to X-ray radiation emitted by said anode, and
   cooling means for cooling at least said anode, said cooling means are arranged using pressurized gas as a coolant medium, said cooling means comprising at least one supply passageway for supplying said pressurized gas towards said anode and at least one exhaust passageway for exhausting said pressurized gas from said anode, said supply passageway and said exhaust passageway being interconnected by means of an expansion chamber surrounding at least partly said anode.

2. The miniature X-ray source device according to claim 1, wherein said at least one exhaust passageway is accommodated in one or more helical X-ray transparent windings around said vacuum tube.

3. The miniature X-ray source device according to claim 1, characterized in that wherein said cooling means comprise two supply passageways.

4. The miniature X-ray source device according to claim 3, wherein said at least one supply passageway has an outer diameter of 0.2–0.01 mm and an inner diameter of 0.17–0.005 mm.

5. The miniature X-ray source device according to claim 1, wherein said exhaust passageway is formed by an interstice present between said housing and said vacuum tube.

6. The miniature X-ray source device according to claim 5, wherein said interstice at least partly surrounds said vacuum tube.

7. The miniature X-ray source device according to claim 5, wherein said interstice at least partly surrounds said at least one supply passageway.

8. The miniature X-ray source device according to claim 1, wherein a thermo-sensor is positioned near said anode to monitor the temperature of the anode.

9. The miniature X-ray source device according to claim 1, wherein a thermo-sensor is positioned near said cathode to monitor the temperature of the cathode.

10. The miniature X-ray source device according to claim 8, wherein wherein said thermo-sensor is one of the group of a miniaturized thermocouple, diode or transistor device.

11. The miniature X-ray source device according to claim 1, wherein said gas is selected from a group consisting of argon (Ar), nitrogen ($N_2$), air, krypton (Kr), $CF_4$, Xenon (Xe) and $N_2O$.

12. The miniature X-ray source device according to claim 1, wherein said electron freeing means comprise an optical fiber connecting said cathode to a light emitting source.

13. The miniature X-ray source device according to claim 12, wherein said light emitting source is controllable.

14. The miniature X-ray source device according to claim 12 or 13, wherein said light emitting source is a laser device, a LED or the like.

15. The miniature X-ray source device according to claim 1, wherein said electric field means comprises a high-voltage conductor connecting said cathode to a high voltage supply and said anode to ground potential.

16. The miniature X-ray source device according to claim 12 or 15, wherein said high voltage conductor is embedded in said optical fibre.

17. The miniature X-ray source device according to claim 1, characterized in that wherein said electron freeing means are part of said electric field means.

18. The miniature X-ray source device according to claim 1, wherein said cathode is of a field emitting type cathode.

19. The miniature X-ray source device to according to claim 1, wherein said cathode is a cold cathode.

20. The miniature X-ray source device according to claim 19, wherein said cathode is a cold cathode made of carbon nanotube material.

21. The miniature X-ray source device according to claim 1, wherein said cathode is a filament made of an electric conducting material.

22. The miniature X-ray source device according to claim 1, wherein said vacuum tube further comprises a Wehnelt cylinder mounted around said cathode.

23. The miniature X-ray source device according to claim 1, wherein said vacuum tube further comprises a getter material.

24. The miniature X-ray source device according to claim 1, wherein said vacuum tube is made of alumina, sapphire, diamond or silica.

25. The miniature X-ray source device according to claim 1, wherein said X-ray source device further comprising control means for controlling said electric field generating means, said electron freeing means and said supply of pressurized gas towards the anode.

26. The miniature X-ray source device according to claim 25, wherein said control means arranged to control the temperature of said cathode and/or anode using said electric field generating means, said electron freeing means, said supply of pressurized gas and said thermo-sensors.

27. A method for effecting radiation therapy comprising:
 exposing an animal body to a miniature X-ray source device according to claim 1.

* * * * *